(12) United States Patent
Zajac et al.

(10) Patent No.: US 10,251,686 B2
(45) Date of Patent: Apr. 9, 2019

(54) ADJUSTABLE SUTURE-BUTTON CONSTRUCT FOR ANKLE SYNDESMOSIS REPAIR

(71) Applicant: ARTHREX, INC., Naples, FL (US)

(72) Inventors: Eric S. Zajac, Naples, FL (US); Ricardo Albertorio, Naples, FL (US); Brandon L. Roller, Naples, FL (US)

(73) Assignee: ARTHREX, INC., Naples, FL (US)

( * ) Notice: Subject to any disclaimer, the term of this patent is extended or adjusted under 35 U.S.C. 154(b) by 635 days.

(21) Appl. No.: 14/883,890

(22) Filed: Oct. 15, 2015

(65) Prior Publication Data
US 2016/0030035 A1   Feb. 4, 2016

Related U.S. Application Data

(63) Continuation of application No. 13/298,863, filed on Nov. 17, 2011, now Pat. No. 9,179,950.
(Continued)

(51) Int. Cl.
*A61B 17/04* (2006.01)
*A61B 17/80* (2006.01)
(Continued)

(52) U.S. Cl.
CPC ...... *A61B 17/8061* (2013.01); *A61B 17/0401* (2013.01); *A61B 17/0469* (2013.01);
(Continued)

(58) Field of Classification Search
CPC . A61B 17/0401; A61B 17/0496; A61B 17/80; A61B 2017/0404
See application file for complete search history.

(56) References Cited

U.S. PATENT DOCUMENTS 2,765,787 A   10/1956 Pellet
3,176,316 A   4/1965 Bodell
(Continued)

FOREIGN PATENT DOCUMENTS

DE   29910202 U1   9/1999
DE   20101791 U1   6/2001
(Continued)

OTHER PUBLICATIONS

E.P. Su, et al., "Using Suture Anchors for Coracoclavicular Fixation in Treatment of Complete Acromioclavicular Separation," The American Journal of Orthopedics, May 2004, pp. 256-257.

*Primary Examiner* — Julie A Szpira
(74) *Attorney, Agent, or Firm* — Carlson, Gaskey & Olds

(57) ABSTRACT

An adjustable, knotless button/loop construct for fixation of ankle syndesmosis tibio-fibular diastasis and an associated method of ankle repair using the same. The knotless construct comprises a pair of buttons attached to a flexible, continuous, self-cinching, adjustable loop integrated with two splices that are interconnected. The knotless construct is passed through fibular and tibia tunnels and the buttons are secured on the cortical surfaces of tibia and fibula. One of the buttons (for example, an oblong button) is secured on the medial side of the tibia by passing the button and the flexible, adjustable loop though the fibular and tibia tunnels and then flipping and seating the button outside the tibia. The length of the flexible adjustable loop is adjusted so that the second button (for example, a round button) is appropriately secured on the lateral fibula.

19 Claims, 14 Drawing Sheets

Related U.S. Application Data

(60) Provisional application No. 61/414,706, filed on Nov. 17, 2010.

(51) Int. Cl.
    *A61B 17/84* (2006.01)
    *A61B 17/86* (2006.01)

(52) U.S. Cl.
    CPC ............ *A61B 17/80* (2013.01); *A61B 17/809* (2013.01); *A61B 17/842* (2013.01); *A61B 17/86* (2013.01); *A61B 2017/0404* (2013.01); *A61B 2017/0477* (2013.01)

(56) References Cited

U.S. PATENT DOCUMENTS

| | | | |
|---|---|---|---|
| 4,187,558 A | 2/1980 | Dahlen et al. | |
| 4,301,551 A | 11/1981 | Dore et al. | |
| 4,400,833 A | 8/1983 | Kurland | |
| 4,776,851 A | 10/1988 | Bruchman et al. | |
| 4,790,850 A | 12/1988 | Dunn et al. | |
| 4,792,336 A | 12/1988 | Hlavacek et al. | |
| 4,851,005 A | 7/1989 | Hunt et al. | |
| 4,863,471 A | 9/1989 | Mansat | |
| 4,917,700 A | 4/1990 | Aikins | |
| 4,932,972 A | 6/1990 | Dunn et al. | |
| 4,988,351 A | 1/1991 | Paulos et al. | |
| 5,024,669 A | 6/1991 | Peterson et al. | |
| 5,026,398 A | 6/1991 | May et al. | |
| 5,129,902 A | 7/1992 | Goble et al. | |
| 5,171,274 A | 12/1992 | Fluckiger et al. | |
| 5,211,647 A | 5/1993 | Schmieding | |
| 5,217,495 A | 6/1993 | Kaplan et al. | |
| 5,219,359 A | 6/1993 | McQuilkin et al. | |
| 5,263,984 A | 11/1993 | Li et al. | |
| 5,266,075 A | 11/1993 | Clark et al. | |
| 5,306,290 A | 4/1994 | Martins et al. | |
| 5,306,301 A | 4/1994 | Graf et al. | |
| 5,320,626 A | 6/1994 | Schmieding | |
| 5,397,357 A | 3/1995 | Schmieding et al. | |
| 5,409,490 A | 4/1995 | Ethridge et al. | |
| 5,562,669 A | 10/1996 | McGuire | |
| 5,575,819 A | 11/1996 | Amis et al. | |
| 5,628,756 A | 5/1997 | Barker et al. | |
| 5,643,266 A | 7/1997 | Li et al. | |
| 5,645,588 A | 7/1997 | Graf et al. | |
| 5,830,234 A | 11/1998 | Wojciechowicz et al. | |
| 5,921,986 A * | 7/1999 | Bonutti ............ | A61B 17/0401 |
| | | | 606/215 |
| 5,931,869 A | 8/1999 | Boucher et al. | |
| 5,961,520 A | 10/1999 | Beck, Jr. et al. | |
| 5,964,764 A | 10/1999 | West et al. | |
| 6,056,752 A | 5/2000 | Roger | |
| 6,099,530 A | 8/2000 | Simonian et al. | |
| 6,099,568 A | 8/2000 | Simonian et al. | |
| 6,110,207 A | 8/2000 | Eichhorn et al. | |
| 6,117,160 A * | 9/2000 | Bonutti ............ | A61B 17/0401 |
| | | | 606/215 |
| 6,159,234 A | 12/2000 | Bonutti et al. | |
| 6,193,754 B1 | 2/2001 | Seedhom | |
| 6,203,572 B1 | 3/2001 | Johnson et al. | |
| 6,238,395 B1 | 5/2001 | Bonutti | |
| 6,283,996 B1 | 9/2001 | Chervitz et al. | |
| 6,296,659 B1 | 10/2001 | Foerster | |
| 6,325,804 B1 | 12/2001 | Wenstrom, Jr. et al. | |
| 6,517,578 B2 | 2/2003 | Hein | |
| 6,533,802 B2 | 3/2003 | Bojarski et al. | |
| 6,635,073 B2 | 10/2003 | Bonutti | |
| 6,641,596 B1 | 11/2003 | Lizardi et al. | |
| 6,716,234 B2 | 4/2004 | Grafton et al. | |
| 7,097,654 B1 | 8/2006 | Freedland | |
| 7,235,091 B2 * | 6/2007 | Thornes ............ | A61B 17/0401 |
| | | | 606/232 |
| 7,494,506 B2 | 2/2009 | Brulez et al. | |
| 7,686,838 B2 | 3/2010 | Wolf et al. | |
| 7,749,250 B2 | 7/2010 | Stone et al. | |
| 7,776,039 B2 | 8/2010 | Bernstein et al. | |
| 7,819,898 B2 | 10/2010 | Stone et al. | |
| 7,828,855 B2 | 11/2010 | Ellis et al. | |
| 7,875,057 B2 * | 1/2011 | Cook ....................... | A61D 1/00 |
| | | | 128/898 |
| 7,875,058 B2 * | 1/2011 | Holmes, Jr. ......... | A61B 17/0401 |
| | | | 606/232 |
| 7,905,903 B2 | 3/2011 | Stone et al. | |
| 7,914,539 B2 | 3/2011 | Stone et al. | |
| 8,109,965 B2 | 2/2012 | Stone et al. | |
| 8,118,836 B2 | 2/2012 | Denham et al. | |
| 8,162,997 B2 | 4/2012 | Struhl | |
| 8,206,446 B1 | 6/2012 | Montgomery | |
| 8,231,654 B2 | 7/2012 | Kaiser et al. | |
| 8,388,655 B2 | 3/2013 | Fallin et al. | |
| 8,512,376 B2 | 8/2013 | Thornes | |
| 8,821,551 B2 | 9/2014 | Zeetser et al. | |
| 9,259,217 B2 | 2/2016 | Fritzinger et al. | |
| 2001/0041938 A1 | 11/2001 | Hein | |
| 2002/0019634 A1 * | 2/2002 | Bonutti ............... | A61B 17/0401 |
| | | | 606/60 |
| 2002/0161439 A1 | 10/2002 | Strobel et al. | |
| 2002/0198527 A1 | 12/2002 | Muckter | |
| 2003/0114929 A1 | 6/2003 | Knudsen et al. | |
| 2003/0130694 A1 | 7/2003 | Bojarski et al. | |
| 2003/0236555 A1 * | 12/2003 | Thornes ............. | A61B 17/0401 |
| | | | 606/232 |
| 2004/0015171 A1 | 1/2004 | Bojarski et al. | |
| 2004/0059415 A1 | 3/2004 | Schmieding | |
| 2004/0073306 A1 | 4/2004 | Eichhorn et al. | |
| 2004/0116963 A1 | 6/2004 | Lattouf | |
| 2004/0236373 A1 | 11/2004 | Anspach, III | |
| 2004/0243235 A1 | 12/2004 | Goh et al. | |
| 2004/0267360 A1 | 12/2004 | Huber | |
| 2005/0004670 A1 | 1/2005 | Gebhardt et al. | |
| 2005/0033363 A1 | 2/2005 | Bojarski et al. | |
| 2005/0065533 A1 | 3/2005 | Magen et al. | |
| 2005/0070906 A1 | 3/2005 | Clark et al. | |
| 2005/0137704 A1 | 6/2005 | Steenlage | |
| 2005/0149187 A1 | 7/2005 | Clark et al. | |
| 2005/0171603 A1 | 8/2005 | Justin et al. | |
| 2005/0203623 A1 | 9/2005 | Steiner et al. | |
| 2005/0261766 A1 | 11/2005 | Chervitz et al. | |
| 2006/0067971 A1 | 3/2006 | Story et al. | |
| 2006/0095130 A1 | 5/2006 | Caborn et al. | |
| 2006/0142769 A1 | 6/2006 | Collette | |
| 2006/0190041 A1 | 8/2006 | Fallin et al. | |
| 2006/0264944 A1 * | 11/2006 | Cole .................... | A61B 17/683 |
| | | | 606/62 |
| 2006/0265064 A1 | 11/2006 | Re et al. | |
| 2007/0021839 A1 | 1/2007 | Lowe | |
| 2007/0083236 A1 | 4/2007 | Sikora et al. | |
| 2007/0118217 A1 | 5/2007 | Brulez | |
| 2007/0162123 A1 | 7/2007 | Whittaker et al. | |
| 2007/0162125 A1 | 7/2007 | LeBeau et al. | |
| 2007/0179531 A1 | 8/2007 | Thornes | |
| 2007/0225805 A1 | 9/2007 | Schmieding | |
| 2007/0239209 A1 | 10/2007 | Fallman | |
| 2007/0239275 A1 | 10/2007 | Willobee | |
| 2007/0250163 A1 | 10/2007 | Cassani | |
| 2007/0270857 A1 | 11/2007 | Lombardo et al. | |
| 2008/0046009 A1 | 2/2008 | Albertorio et al. | |
| 2008/0082128 A1 * | 4/2008 | Stone .................. | A61B 17/0401 |
| | | | 606/232 |
| 2008/0177302 A1 * | 7/2008 | Shurnas ............. | A61B 17/0401 |
| | | | 606/228 |
| 2008/0188935 A1 | 8/2008 | Saylor et al. | |
| 2008/0188936 A1 | 8/2008 | Ball et al. | |
| 2008/0195148 A1 | 8/2008 | Cook et al. | |
| 2008/0208252 A1 * | 8/2008 | Holmes ............. | A61B 17/0401 |
| | | | 606/232 |
| 2008/0215150 A1 | 9/2008 | Koob et al. | |
| 2008/0228271 A1 | 9/2008 | Stone et al. | |
| 2008/0234819 A1 | 9/2008 | Schmieding et al. | |
| 2008/0243248 A1 | 10/2008 | Stone et al. | |
| 2008/0275553 A1 | 11/2008 | Wolf et al. | |

(56) References Cited

U.S. PATENT DOCUMENTS

| | | |
|---|---|---|
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0036893 A1 | 2/2009 | Kartalian et al. |
| 2009/0054982 A1 | 2/2009 | Cimino |
| 2009/0062854 A1 | 3/2009 | Kaiser et al. |
| 2009/0082805 A1 | 3/2009 | Kaiser et al. |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0224729 A1 | 9/2011 | Baker et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0282350 A1 | 11/2011 | Kowarsch et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0150297 A1* | 6/2012 | Denham ............ A61B 17/0401 623/13.14 |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |
| 2013/0331886 A1 | 12/2013 | Thornes |
| 2017/0209140 A1 | 7/2017 | Thornes |

FOREIGN PATENT DOCUMENTS

| | | |
|---|---|---|
| EP | 0440991 A1 | 8/1991 |
| EP | 1108401 A1 | 6/2001 |
| EP | 1707127 A1 | 10/2006 |
| EP | 2238944 A2 | 10/2010 |
| WO | 2007/002561 A1 | 1/2007 |
| WO | 2008/091690 A1 | 7/2008 |

* cited by examiner

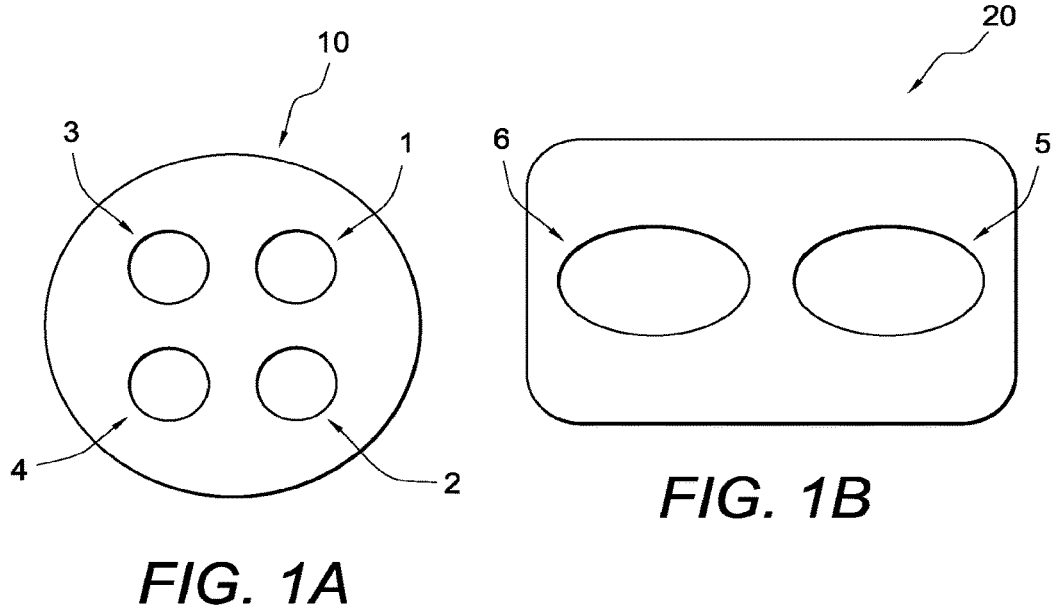

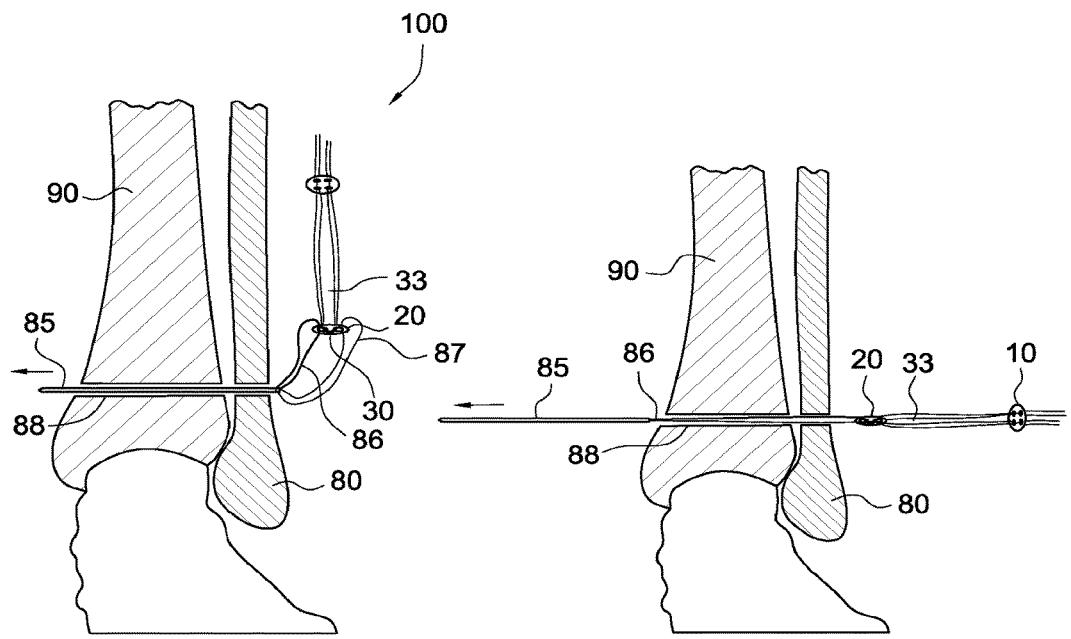
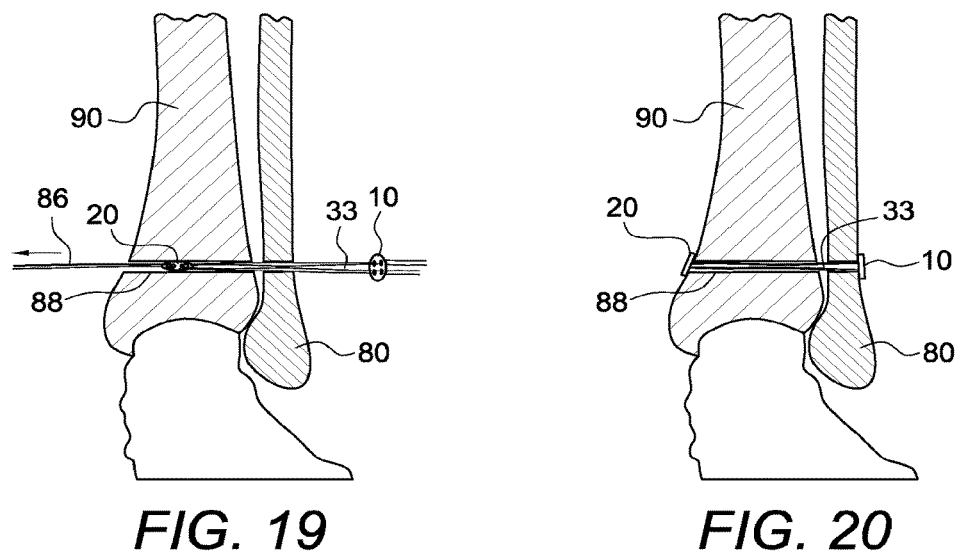

ADJUSTABLE SUTURE-BUTTON CONSTRUCT FOR ANKLE SYNDESMOSIS REPAIR

CROSS-REFERENCE TO RELATED APPLICATIONS

This application is a continuation of U.S. patent application Ser. No. 13/298,863, filed Nov. 17, 2011, now U.S. Pat. No. 9,179,950 which claims the benefit of U.S. Provisional Application No. 61/414,706, filed Nov. 17, 2010, the entire disclosures of which are incorporated herein by reference.

FIELD OF THE INVENTION

The present invention relates to the field of ankle surgery and, more particularly, to ankle syndesmosis repair techniques and associated fixation and reconstruction devices.

BACKGROUND OF THE INVENTION

Ankle injuries are among the most common of the bone and joint injuries. The ankle joint is formed of three bones coming together: the tibia which makes up the medial, or inside, anklebone; the fibula which parallels the tibia and makes up the lateral, or outside, anklebone; and the talus. The far ends of the tibia and fibula are known as the malleoli and together they form an arch that sits on top of the talus.

A fibrous membrane (the joint capsule) encases the joint architecture and is lined with a smoother layer called the synovium. The joint capsule contains the synovial fluid produced by the synovium. The synovial fluid allows for smooth movement of the joint surfaces. The ankle joint is stabilized by three groups of ligaments, which are fibers that hold these bones in place.

Surgery to fix an ankle fracture is indicated for patients who suffer a displaced ankle fracture involving the bone on the inside to the ankle (tibia), the bone on the outside of the ankle (fibula), or both. One injury that may occur in the ankle is a disruption of the syndesmosis. A syndesmotic injury is a disruption of the strong fibrous ligaments that hold the fibula and tibia together near the ankle joint. If the syndesmosis is disrupted, then the ankle joint will be unstable and surgery is usually indicated.

A suture-button construct for ankle syndesmosis repair is the subject matter of U.S. Pat. No. 7,235,091, the disclosure of which is incorporated by reference herein in its entirety. The construct and technique disclosed in this prior patent greatly facilitates ankle syndesmosis repair as compared to the prior art, but it requires the tying of knots to secure the second (round) button against the surface of the lateral fibular cortex. An ankle syndesmosis repair construct and technique is needed which provides the same fixation as disclosed in the aforementioned patent, but without the need for tying knots.

SUMMARY OF THE INVENTION

The present invention provides methods and reconstruction systems (an adjustable, self-locking knotless button/loop construct) for ankle syndesmosis with or without associated ankle fractures repair. One embodiment system of the present invention comprises an adjustable, knotless button/loop construct formed of a pair of fixation devices (for example, two buttons) connected by an adjustable, knotless flexible loop. Another embodiment system of the present invention comprises an adjustable, knotless button/loop construct interlocked with a non-adjustable loop each attached to a fixation device (for example, two buttons. The loop includes a flexible material (preferably suture or suture tape), for fracture fixation when a plate is disposed between the fractured bone and one fixation device.

The present invention also provides a method of assembling an adjustable self-locking, knotless button/loop construct by inter alia: (i) providing two fixation devices (i.e., an oblong button and a round button); (ii) threading a flexible strand through holes of the first and second button, to form a braid loop and an intertwining or interlinking "x" of the braid on the round button; (iii) forming two adjustable eyesplices on the braid loop and through the oblong button, so that the oblong button is centered between the two spliced sections; and (iv) threading the tails through the top holes of the round button.

The present invention also provides a method of ankle syndesmosis repair by inter alia: (i) providing an ankle repair system comprising an adjustable, self-locking knotless button/loop construct including two fixation devices (for example, a round button and an oblong button), and at least one flexible, adjustable loop attached to the fixation devices (i.e., the buttons); and (ii) securing the repair system to misaligned bones of the ankle.

The present invention also provides a method of ankle syndesmosis repair by inter alia: (i) providing an ankle repair system comprising an adjustable, self-locking knotless button/loop construct including two fixation devices (for example, a round button and an oblong button), and at least one flexible, adjustable loop attached to one fixation devices (i.e., the buttons) and a non-adjustable loop connected to the second fixation device; and (ii) securing the repair system to misaligned bones of the ankle.

The present invention also provides a fracture management system by inter alia: (i) providing an ankle repair system comprising an adjustable, self-locking knotless button/loop construct including two fixation devices (for example, a round button and an oblong button), and at least one flexible, adjustable loop attached to the fixation devices (i.e., the buttons); (ii) providing a fracture plate, and (iii) securing the repair system and plate to misaligned and fractured bones of the ankle.

These and other features and advantages of the present invention will become apparent from the following description of the invention that is provided in connection with the accompanying drawings and illustrated embodiments of the invention.

BRIEF DESCRIPTION OF THE DRAWINGS

FIGS. 1A and 1B illustrate a schematic top view of a round button and an oblong (elongated) button of an adjustable, self-locking knotless button/loop construct of the present invention.

FIG. 2 illustrates the braid strand passed through holes 1 and 2 of the round button of FIG. 1A.

FIGS. 17-20 illustrate subsequent steps of a method of ankle syndesmosis repair employing the self-locking, knotless button/loop construct of FIG. 16 and according to the present invention.

DETAILED DESCRIPTION

The present invention provides assembling steps and reconstruction systems for the stabilization of ankle bones (for ankle syndesmosis repair) using an adjustable, knotless button/loop construct in a minimally invasive approach.

The stabilization system of the present invention comprises a knotless button/loop construct including two fixation devices (for example, two buttons) and at least one flexible, adjustable loop attached to the two fixation devices (i.e., the buttons). The knotless button/loop construct has an adjustable loop length and allows adjustment in one direction while preventing or locking the construct from loosening in the opposite direction, due to applied tensile forces.

The present invention also provides a method of ankle repair by inter alia: (i) providing a button/loop construct with two buttons and at least one flexible, adjustable loop (a four-point knotless fixation device) that is capable of adjusting tension (i.e., is provided with a loop having an adjustable perimeter and length) attached to the buttons; and (ii) securing the ankle bones in the proper position by advancing the button/loop construct through tunnels formed within the ankle bones.

Figure 15:
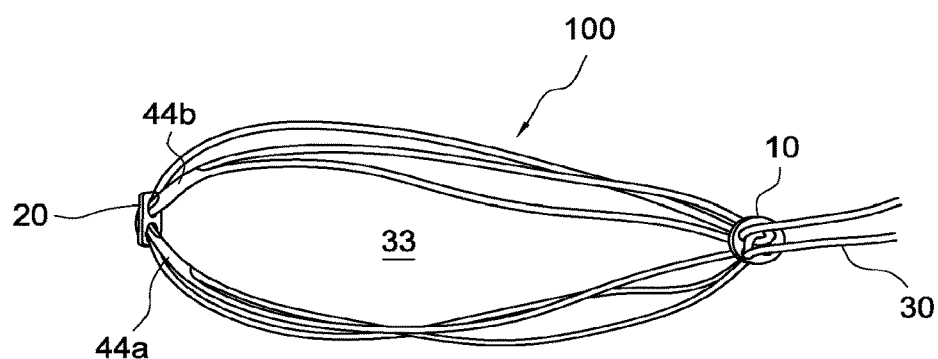
FIG. 15 illustrates the final construct (adjustable, self-locking knotless button/loop construct) of the present invention.
Figure 16:
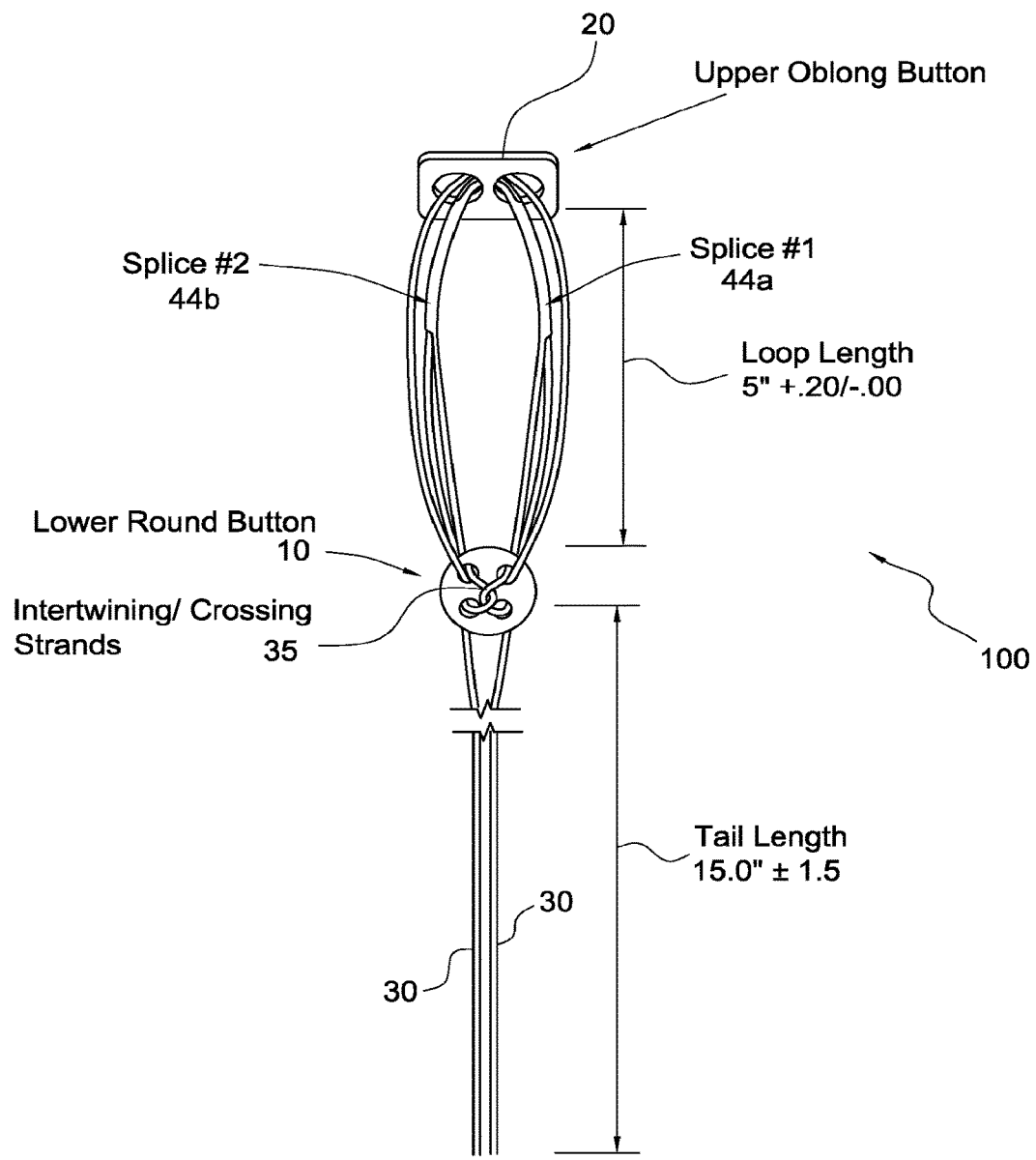
FIG. 16 is another, schematic view of the final, assembled, self-locking, knotless button/loop construct of the present invention (with a knotless, self-locking, loop attached to a round button and an oblong button, and with two splices through the oblong button, and intertwining/crossing strands on the round button).
Figure 21:
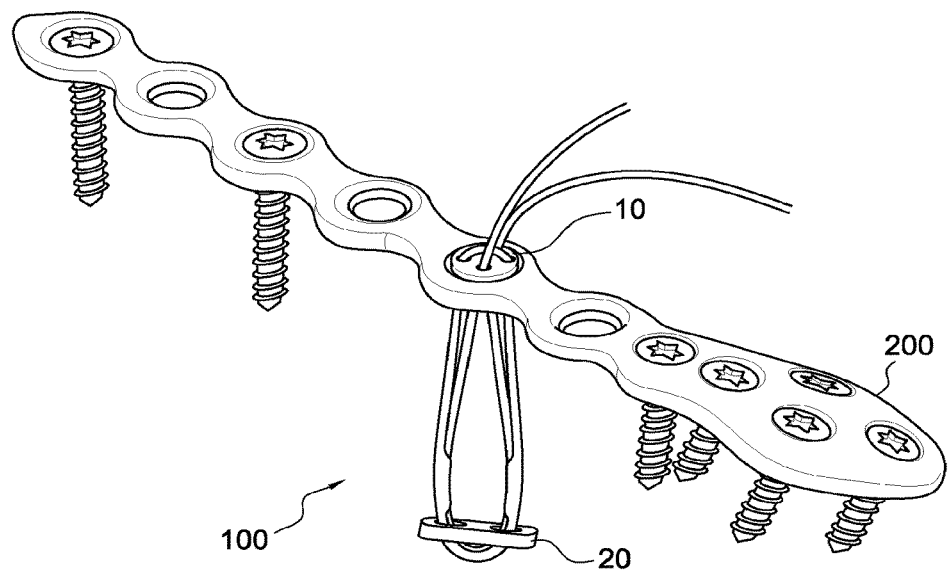
FIG. 21 illustrates a fracture fixation plate with self-locking, knotless button/loop construct of FIG. 16.
Figure 22:
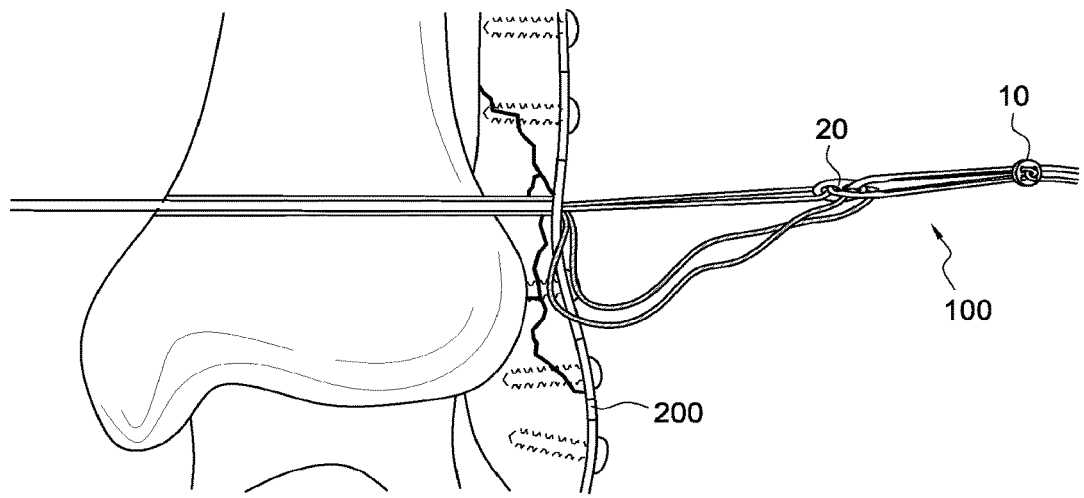
FIGS. 22-26 illustrate subsequent steps of a method of ankle syndesmosis repair and fracture fixation employing the self-locking, knotless button/loop construct of FIG. 16 and the fixation plate of FIG. 21.
Figure 23:
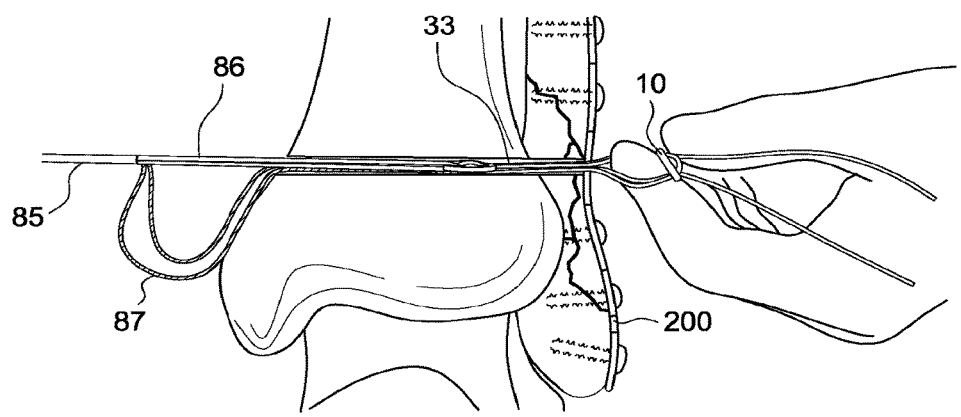
Figure 24:
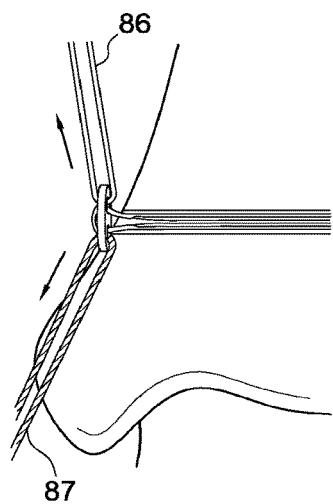
Figure 25:
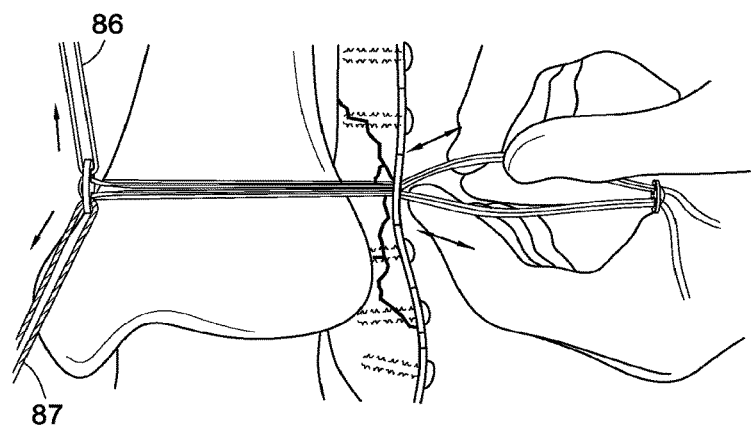
Figure 26:
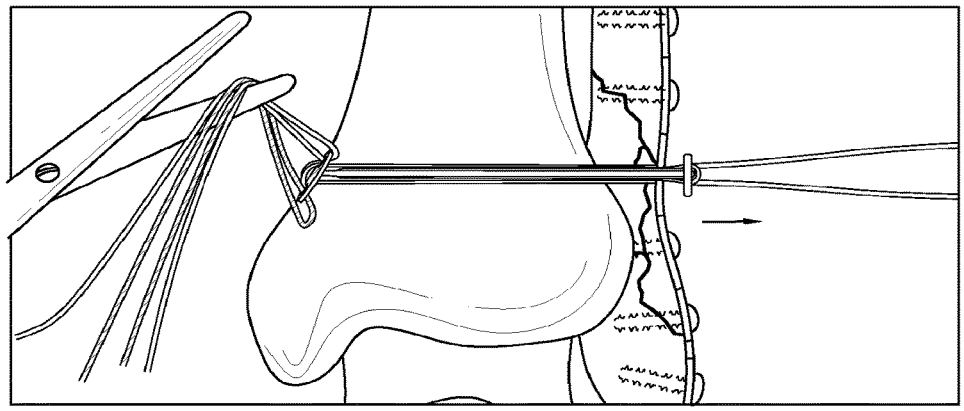
Figure 27:
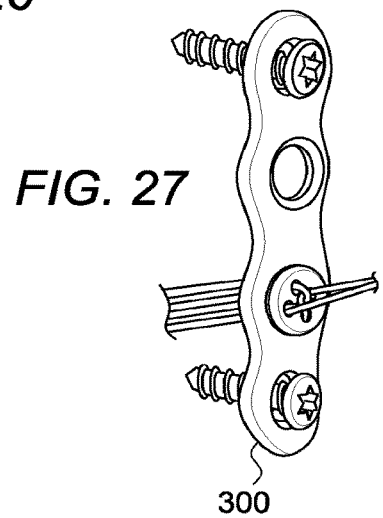
FIG. 27 illustrates a buttress plate with self-locking, knotless button/loop construct of FIG. 16.

Referring now to the drawings, where like elements are designated by like reference numerals, FIG. 1 illustrates top views of two fixation devices 10, 20 (button 10, 20) used for assembling the knotless, integrated, ankle repair system 100 (button/loop construct 100) of the present invention (shown in FIGS. 15 and 16). The knotless repair system 100 is an integrated system comprising two fixation devices 10, 20 attached to at least one flexible, adjustable loop formed of a flexible material 30.

The flexible material 30 forming the loop has an adjustable length and, as described below, is connected to two fixation devices (buttons) that are further secured on tibial cortex and fibular cortex, respectively. The flexible material is threaded through apertures/holes/eyelets of each of the first and second fixation devices 10, 20 and splices are created to form the knotless, integrated, self-cinching ankle repair system 100. In an exemplary only embodiment, and as detailed below, the flexible material 30 may be suture such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others).

In an alternative embodiment, the flexible material 30 may be suture such as FiberWire®, e.g., UHMWPE and polyester braided over a core of UHMWPE, such as #2 FiberWire®.

In an exemplary embodiment only, the first fixation device 10 is a round button provided with four circular holes having a round configuration, and the second fixation device 20 is an oblong button provided with two eyelets 5 and 6 having an oblong or elliptical configuration, or any other configuration including round, teardrop shape, or circular configuration. Although the embodiments below will be detailed with reference to particular configurations for the first and second fixation devices 10, 20 (i.e., a round button and an oblong, elongate button), the invention is not limited to this exemplary embodiment only and has applicability to fixation devices with other shapes and geometries, as long as the fixation devices are provided with apertures/holes/passages that allow a flexible material (a flexible strand) to pass therethrough (or be threaded therethrough) to form the flexible, adjustable, self-cinching, knotless loop of the invention.

FIGS. 2-14 illustrate exemplary steps of a method of assembling the reconstruction system 100 of FIGS. 15 and 16 (with the following starting materials which are only exemplary).

Starting Materials:
Braided high strength (UHMWPE) suture strand 30
Needle with nitinol loop 40
Round button 10
Oblong button 20

Assembly Instructions:
Step 1: A braided strand 30 is inserted through holes 1 and 2 of the round button 10. Fold braid 30 at midpoint to create two parallel equal length strands. FIG. 2 shows the braided strand 30 through holes 1 and 2 of the round button 10. In an exemplary embodiment, braided strand 30 is a braided UHMWPE strand.

Figure 3:
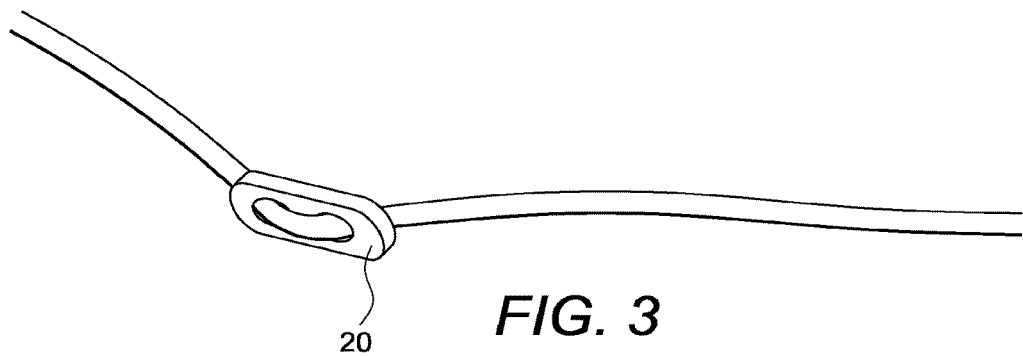
FIG. 3 illustrates the braided strand passed through the eyelet holes of the oblong button of FIG. 1B.

Step 2: One end of the braided strand 30 is inserted through both eyelets 1 and 2 of the oblong button 20. FIG. 3 shows the braided strand 30 through the eyelets 5 and 6.

Figure 4:
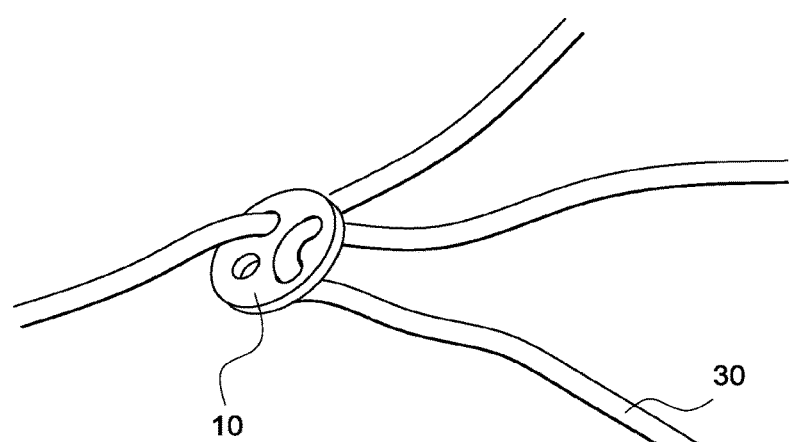
FIG. 4 illustrates the strand passed through hole 3 of the round button.
Figure 5:
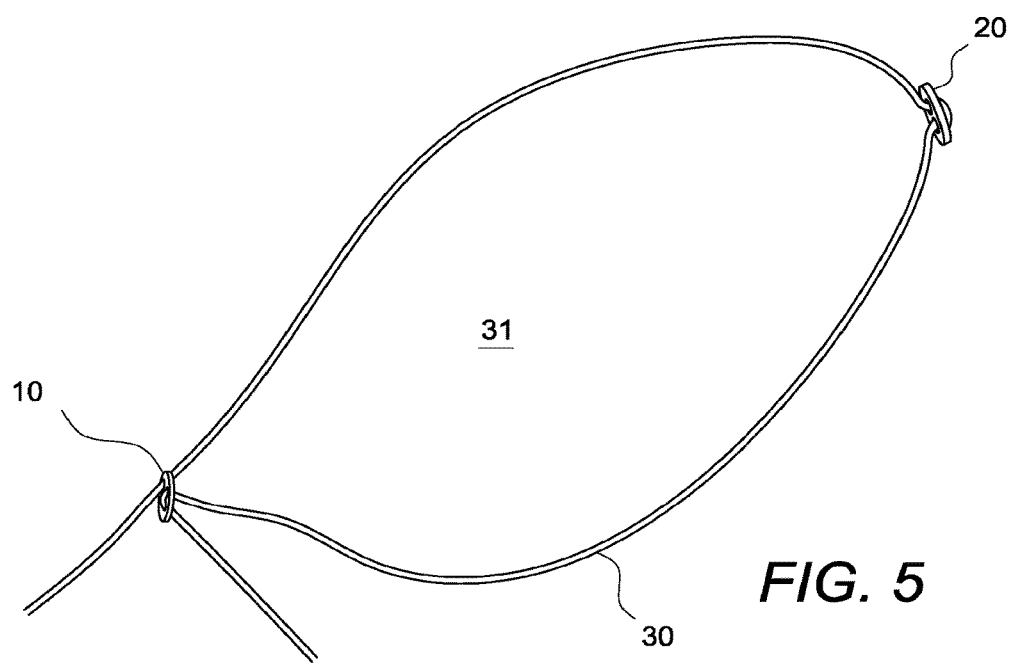
FIG. 5 illustrates the braid loop connecting the round button and the oblong button.

Step 3: The same strand 30 (that passed through oblong button 20) is threaded through hole 3 of the round button 10. This creates a loop 31 (FIG. 5) connecting both buttons 10, 20. FIG. 4 shows the strand 30 through hole 3 of the round button 10, and FIG. 5 shows the braid loop 31 connecting the round button 10 and the oblong button 20.

Figure 6:
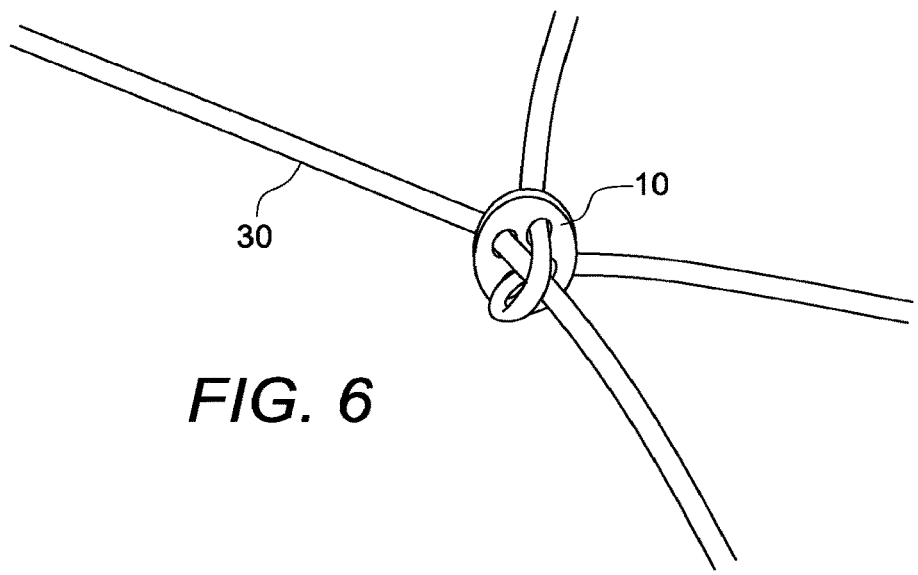
FIG. 6 illustrates the strand from hole 3 passing under the strand bridging holes 1 and 2.

Step 4: The tail of the same strand 30 (that passed through hole 3) is passed under the strand looped through holes 1 and 2. FIG. 6 shows the strand from hole 3 passing under the strand in holes 5 and 6 of the round button 10. The tail of the same strand 30 is then passed over the strand looped through holes 1 and 2.

Figure 7A:
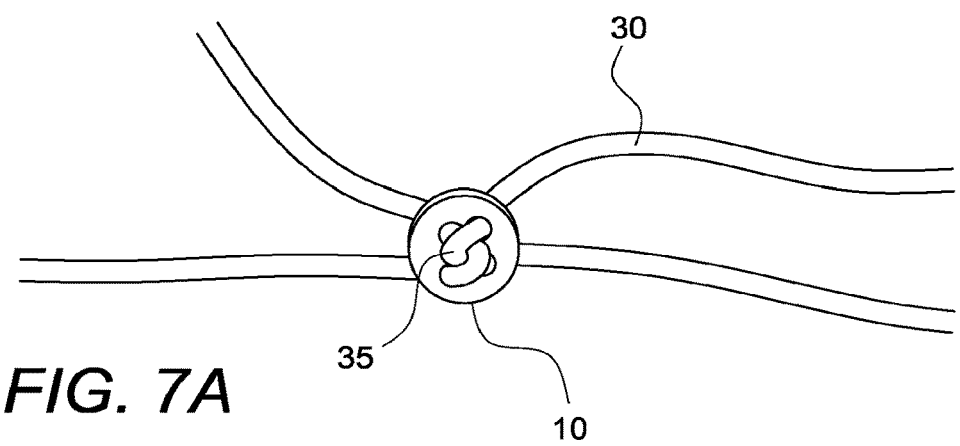
FIGS. 7A and 7B illustrate the intertwined strands forming an "X" on the round button.
Figure 7B:
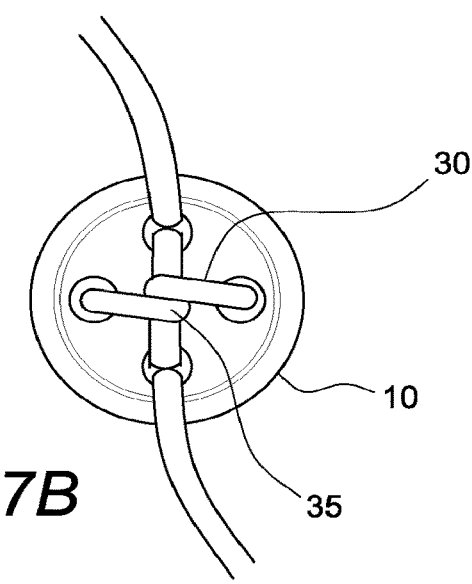

Step 5: The tail of same strand 30 is then threaded down through hole 4. This forms an intertwining or interlinking "X" 35 of the braid 30. The strand looped across holes 1 and 2 will be linked with the strand across holes 3 and 4. FIG. 7A and its schematic representation of FIG. 7B show the intertwined strands forming an "X" structure 35 on the round button 10.

Figure 8:
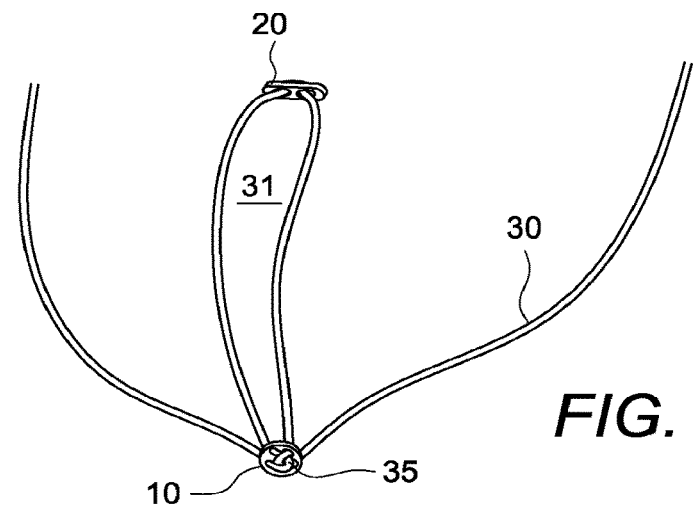
FIG. 8 illustrates the tail strands of each side of the round button pulled towards the oblong button.
Figure 9:
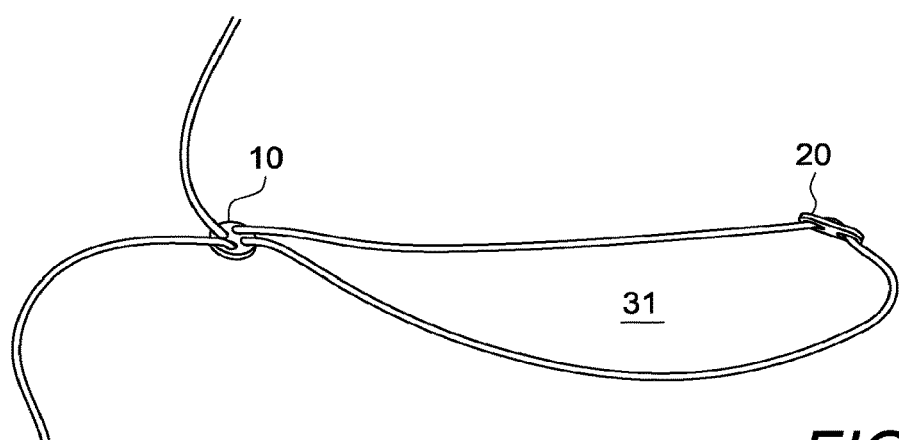
FIG. 9 illustrates the tail strands exiting from holes adjacent to one another on the round button and strands forming a loop through the oblong button exiting from holes adjacent to one another on the round button.
Figure 10:
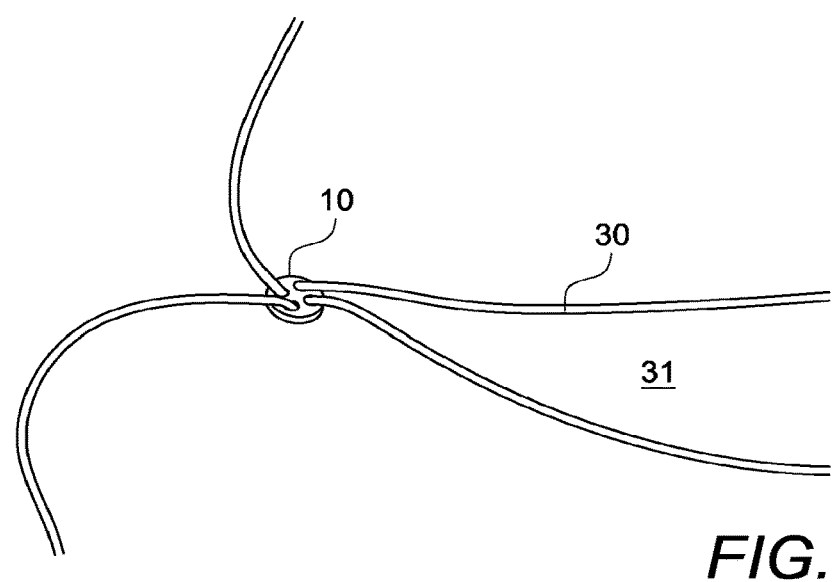
FIG. 10 illustrates an enlarged view of the underside of the round button.

Step 6: The following is confirmed:

a) The tails of each strand are pulled towards the oblong button 20 on each side of the round button 10 (as shown in FIG. 8).

b) Viewing the underside of the round button 10, the tail strands are exiting from holes adjacent to one another (as shown in FIGS. 9 and 10).

c) Viewing the underside of the round button 10, the strands forming the loop 31 through the oblong button 20 are adjacent to one another (as shown in FIGS. 9 and 10).

FIG. 8 shows the tail strands of each side of the round button 10 pulled towards the oblong button 20. FIG. 9 shows the tail strands exiting from holes adjacent to one another on the round button 10 and strands forming loop 31 through the oblong button 20 exiting from holes adjacent to one another on the round button 10. FIG. 10 shows the close up view of the underside of the round button 10.

Figure 11:
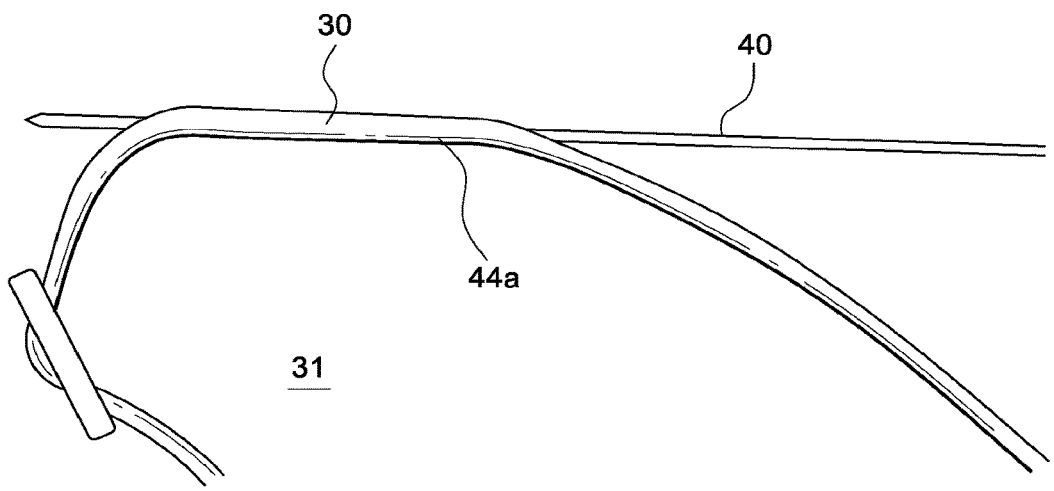
FIG. 11 illustrates an enlarged view of the 0.75" splice (with the oblong button moved to the side to allow splicing near the center of the braided loop formed between the buttons).

Step 7: One tail strand is used to start a splice towards the midpoint of the braid loop 31 at oblong button 20. A splice 44a (FIG. 12) is created by passing the blunt tip needle 40 through the center of the braid 30 with the end of the strand 30 being carried through in the nitinol loop of the needle 40. The oblong button 20 may need to be moved to the side to allow splicing. The splice location should preferably be on the same side as the tail strand making the splice. FIG. 11 shows a close up of splice 44a. The oblong button 20 is moved to the side to allow splicing near center of braided loop 31 formed between buttons 10, 20.

Figure 12:
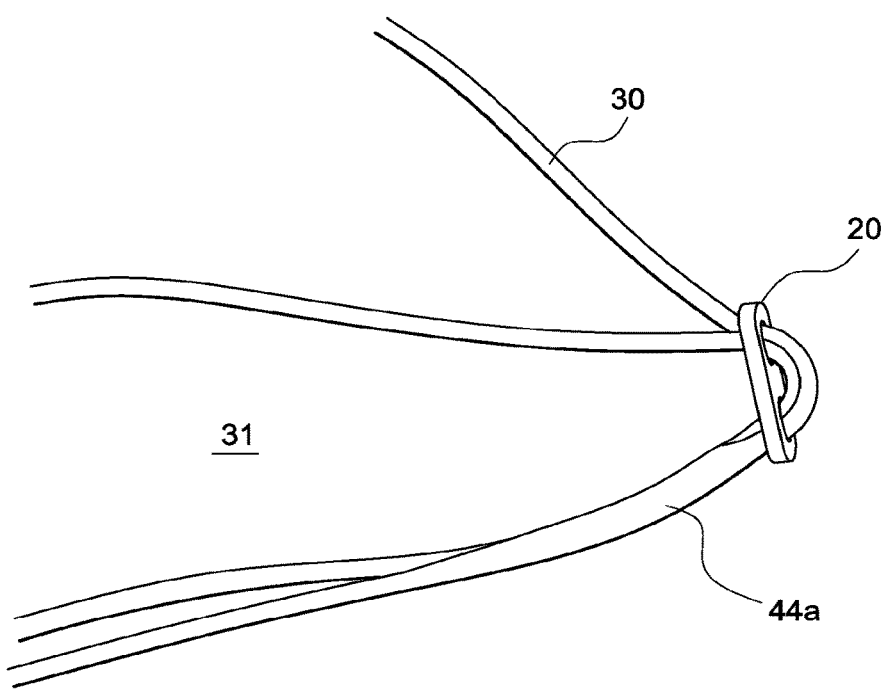
FIG. 12 illustrates a splice on one side with tail passing through the oblong button.

Step 8: After the strand 30 is carried with needle 40 to create the splice 44a, the tail of the strand is threaded through both eyelet holes in the oblong button 20 (in from the bottom and out the top of the button 20). The oblong button 20 is slid so that it rests over spliced section. FIG. 12 shows the splice 44a on one side with the tail passing through the oblong button 20.

Figure 13:
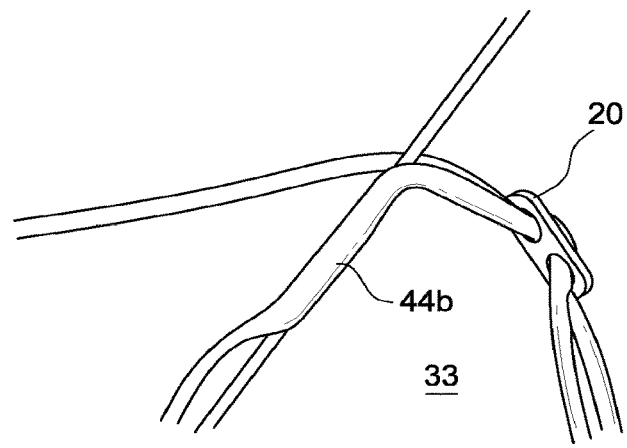
FIG. 13 illustrates the formation of a second splice with the strand exiting at the end of the first splice.

Step 9: Steps 7 and 8 (detailed above) are repeated to create another splice 44b with the opposing strand on the other side. The second splice 44b should be created such that the exiting aperture of the splice is as close as possible to the first splice 44a. The splice length may be about 17-19 mm. The tail of the strand is threaded through both eyelet holes of oblong button 20. FIG. 13 shows the formation of second splice 44b with the strand exiting at end of first splice 44a and as part of knotless, adjustable flexible loop 33.

Step 10: The oblong button 20 is slid to center between the two spliced sections 44a, 44b. The oblong button 20 sits approximately centered between the splices. The lower round button 10 sits approximately centered between intertwining/crossing "X" 35 of the strands.

Figure 14:
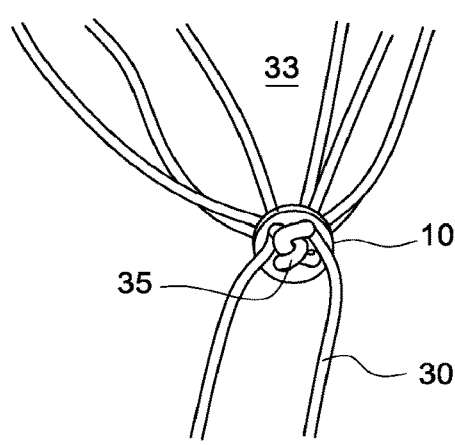
FIG. 14 illustrates the strands passing through top holes 1 and 3 of the round button.

Step 11: The tails of each strand are threaded through the top holes (holes 1 and 3) in the round button 10. Care should be taken to thread the tails through holes on same side of the button 10. Strands should not be crossed or twisted. The result is one overall adjustable knotless loop 33. FIG. 14 shows the strands passing through top holes 1 and 3 of the round button 10.

Step 12: After the button/loop construct 100 is constructed, the construct is stretched. The force to stretch the loop of the construct is applied such that it acts on the overall loop created between the two splices 44a, 44b rather than on individual splice loop.

FIGS. 15 and 16 show the final construct 100. As shown in FIGS. 15 and 16 and as detailed above, button/loop construct 100 (reconstruction system 100) is formed of a pair of buttons 10, 20 connected by a flexible, knotless, adjustable loop 33. Loop 33 includes a flexible material 30 with two adjustable eyesplices 44a, 44b.

In an exemplary and illustrative embodiment only, self-locking, knotless, adjustable button/loop construct 100 includes buttons 10, 20 and flexible material 30 with two adjustable eyesplices 44a, 44b that are interconnected to form one adjustable loop 33. By pulling on the free braid strands 30, the individual eyesplices constrict and, in turn, reduce the loop length of loop 33. Elongation of loop 33 is prevented because for loop 33 to elongate, a force must be applied interior to one or both of the eyesplices to elongate the individual loops.

Details regarding the formation/assembly of a self-locking adjustable construct with only one fixation device and two adjustable discrete splices, each splice (and which allows a graft to be fully inserted and seated in a bone tunnel) are provided in U.S. Patent Application Publication Nos. 2010/0256677 and 2010/0268273, the disclosures of which are incorporated by reference in their entirety herewith.

As described in the above-noted applications, a self-locking, adjustable, knotless construct includes a button and a flexible material with two adjustable eyesplices that are interconnected to form an adjustable continuous loop. By pulling on the free braid strands, the individual eyesplices constrict and, in turn, reduce the loop length L of loop. In order for the loop to elongate, a force needs to be applied interior to one or both of the eyesplices to elongate the individual loops.

Exemplary steps of a method of forming/assembling a self-locking adjustable knotless construct with only one fixation device (i.e., with only one button) and two splices/eyesplices are detailed in the above-noted applications, and include as starting materials a suture strand (for example, 50 inches of braided UHMWPE strand); a needle (for example, a blunt tip needle with nitinol loop) and a button (for example, a 3.5 mm titanium button). The suture strand is folded to create two equal length parallel braid strands. At this step, the braid is folded at the midpoint, 25 inches, to create two parallel equal length braid strands (Step 1). At Step 2, a first eyesplice is created on the first strand of braid by passing the blunt tip needle through the center of the braid with the end of the braid being carried through in the nitinol loop of the needle. The splice should travel for a distance of about 17-19 mm through the braid towards the braid midpoint created in Step 1.

Once the first eyesplice has been formed, at Step 3, the button is slid over the non-spliced strand passing the strand through both button holes. The button is slid so that it rests over the first spliced section. At Step 4, a second eyesplice is formed, similar to the first one, with the opposing strand. The strand should be looped through the first eyesplice loop resulting in two eyesplice loops that are interconnected. Again, the splice length should be between 17-19 mm. The splice should be created such that the exiting aperture of the splice is as close as possible to the first eyesplice.

Buttons 10, 20 of the construct 100 of the present invention may be formed, for example, of metal, PEEK or PLLA. As detailed above, the buttons are provided with openings (apertures, eyelets, holes) that allow the passage of the flexible material 30 to pass thereto.

The flexible material 30 is preferably a braided high strength suture material. The flexible material 30 may be provided with optional colored strands to assist surgeons in distinguishing between suture lengths with the trace and suture lengths without the trace. The flexible material 30 may be also provided in the form of a suture tape, or a combination of suture strand and suture tape, and as desired. The flexible material 30 may be suture such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others). The flexible material 30 may also contain a bioabsorbable material, such as PLLA, one of the other polylactides, or collagen, for example, and/or may be formed of twisted fibers having strands of a contrasting color added to the braided threads, to make the suture more visible during surgical procedures. In exemplary embodiments, flexible material 30 may be a braided suture cover containing strands of a high strength suture material, such as FiberWire® suture, sold by Arthrex, Inc. of Naples, Fla. The tail ends may preferably be coated (for example, tipped with Loctite or other adhesive).

The method of ankle syndesmosis repair using the suture-button construct of the present invention is similar to that disclosed in U.S. Pat. No. 7,235,091, except that, advantageously, no knot tying is required. Instead, the first (oblong) button of the construct is passed (with a suture passing instrument such as a needle) through drill holes passing through the fibula and tibia bones, flipped and secured against the medial tibial cortex, and the second (round) button is then tightened against the lateral fibular cortex simply by cinching the adjustable construct (instead of tying knots).

FIGS. 17-20 illustrate an ankle repair system 100 of the present invention employed in a method of ankle repair (fracture fixation and/or syndesmosis reduction) according to the present invention. A drill hole 88 is formed through tibia 90 and fibula 80. A long straight needle 85 with pull-through sutures 86 and optionally 87, are attached to the repair system 100 and passed through the drill hole 88, to advance the first, leading oblong button 20 substantially horizontally through the drill hole 88, as shown in FIGS. 18 and 19. Slight upward tension should be placed on the white pull-through suture, while placing downward tension on the green/white suture. The button should seat easily along the medial cortex. Once the first, oblong button 20 has exited the medial tibia 90, the angle of traction on the pull-through suture 86, 87 is changed and counter-traction is exerted on the loop 33, in order to flip (pivot) and engage the oblong button 20 against the medial tibial cortex (FIG. 20).

Once the oblong button 20 is anchored, the pull-through suture 88 can be cut and removed. The trailing or second, round button 10 is tightened down on the lateral side by further traction on the free ends of the suture 30 to tighten the adjustable, flexible loop 33 and adjust the tension between the two buttons 10, 20 (FIG. 20). This will further squeeze the syndesmosis but will not over-tighten it.

FIGS. 21, 27 and 30-32 illustrate fixation or buttress plates using the reconstruction system 100, whereas FIGS. 22-26 and 28-29 illustrate assembly steps for attaching reconstruction system 100, after a fracture plate 200, 400, 500, 600 or buttress plate 300 is affixed. FIGS. 22-26 illustrate, drilling all four cortices, 1.5 cm above the ankle joint, in the transmalleolar plane (30.degree. anterior to the coronal plane), using the 3.5 mm Drill Bit. The needle and pull-through sutures 86, 87 are passed along the drill hole and out the intact medial skin. The white 2-0 FiberWire pull-through suture advances the button 20, until it just exits the medial tibial cortex. A number 2.0 FiberWire suture may be added to facilitate placement of button 20. The pull-through sutures are cut where they connect to the needle after passage through the medial skin. The button 20 should seat easily along the medial.

Figure 28:
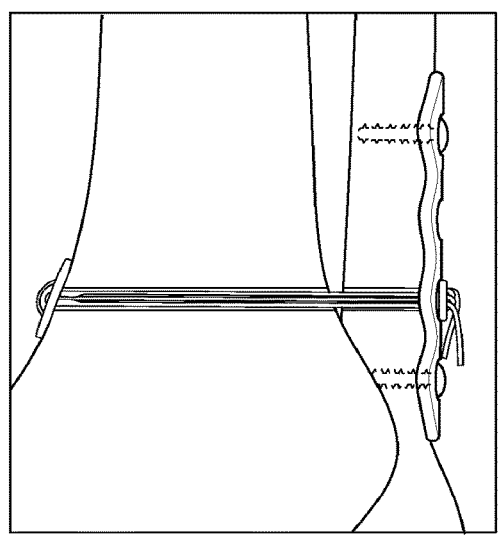
FIGS. 28-29 illustrate subsequent steps of a method of ankle syndesmosis repair employing the self-locking, knotless button/loop construct of FIG. 16 and the buttress plate of FIG. 27, of the present invention.
Figure 29:
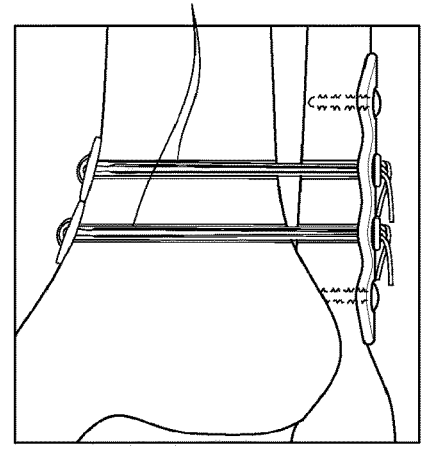
Figure 30:
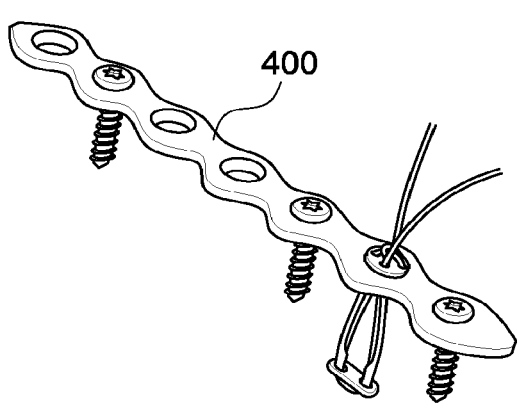
FIG. 30-32 respectively locking straight, tubular and hooking plates with self-locking, knotless button/loop construct of FIG. 16.
Figure 31:
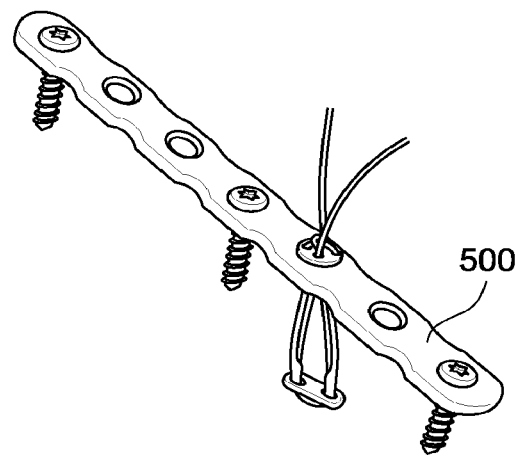
Figure 32:
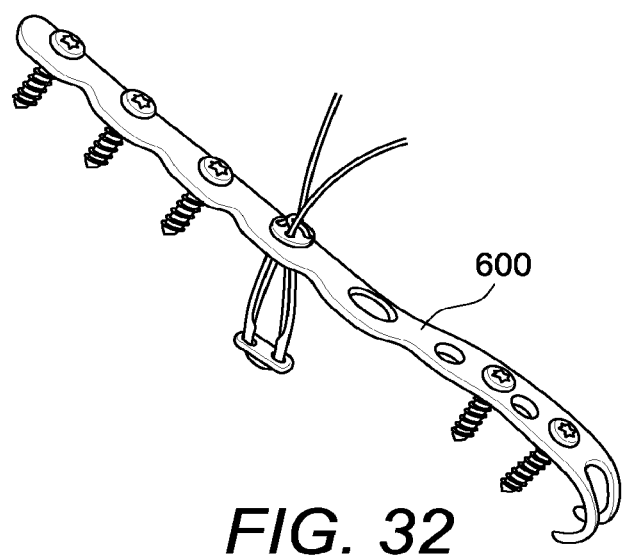

FIGS. 28-29 illustrate attachment of construct 100 of the present invention may with a buttress plate 300 that features a four-hole plate. The contoured, titanium plate is preferably used as a "buttress" for ankle syndesmotic repairs with or without ankle fracture. The plate has two inner holes that custom fit the button 10, and two outer holes that accept two 3.5 mm times.14 mm non-locking screws. The 3.5 mm screws are placed in the proximal and distal holes of the plate and the construct 100 is then placed in either the third hole (6), or both central holes (inset), if desired.

Figure 33:
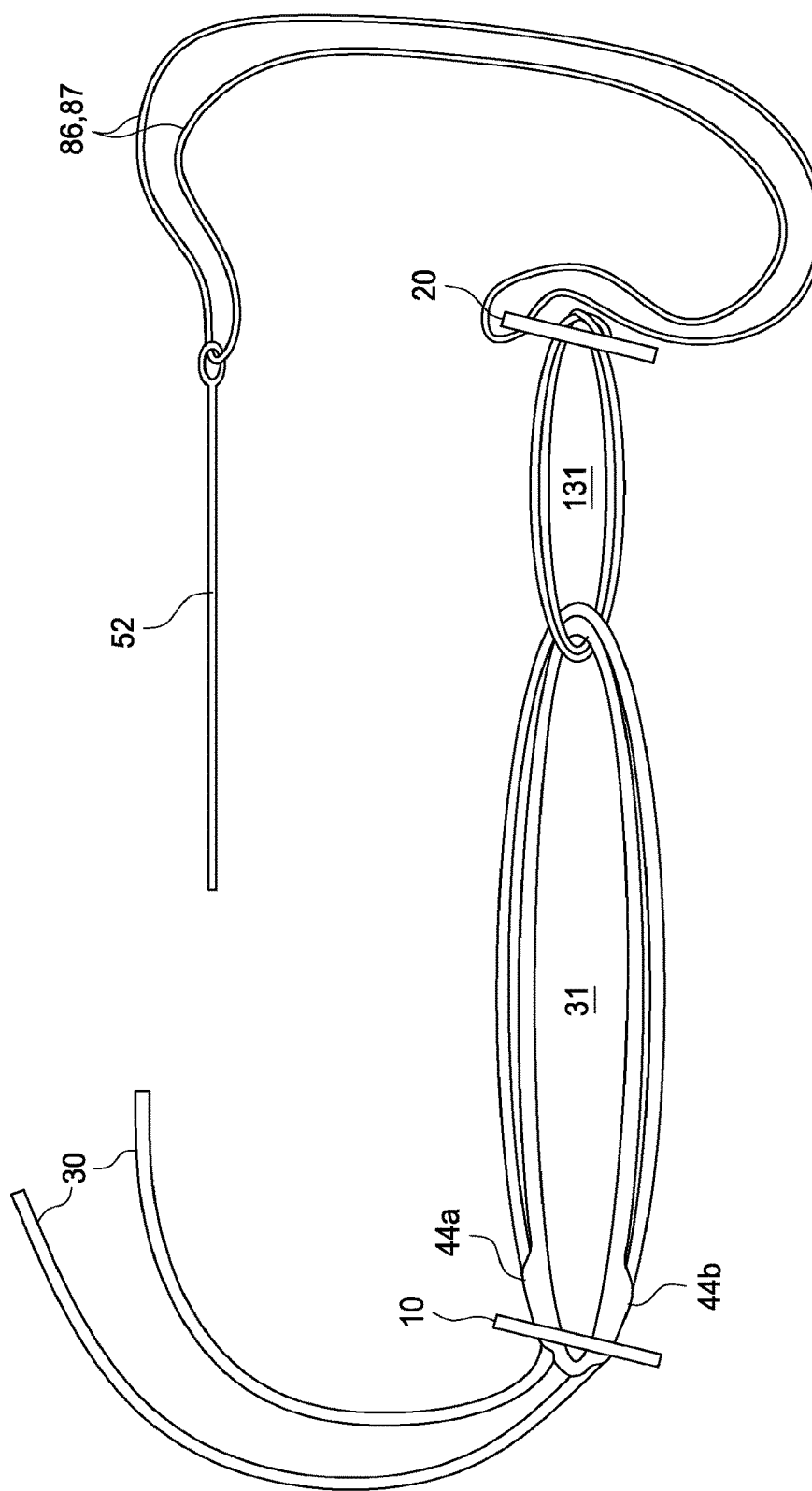
FIG. 33 schematically illustrates another adjustable loop construct in accordance with the present invention.
Figure 34:
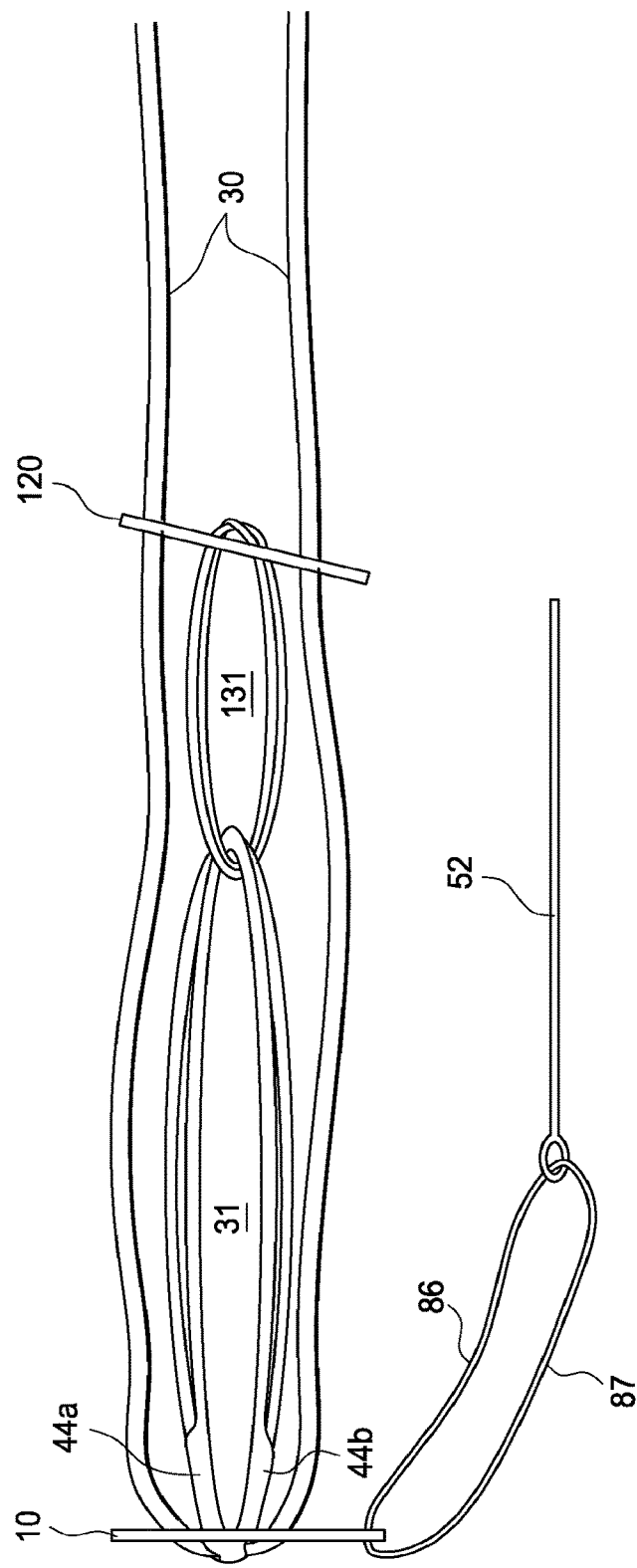
FIG. 34 schematically illustrates a further adjustable loop construct in accordance with the present invention.

FIGS. 33 and 34 schematically illustrate alternative attachment construct embodiments where loop 31 of construct 100 interlocked with a non-adjustable loop 131 of flexible material. The construct embodiment of FIG. 33 is deployed in a manner similar to that illustrated in FIGS. 17-20 when a plate is not needed or used, and FIGS. 22-29 when a plate is used as detailed above. In the construct embodiment of FIG. 34, a 4-hole button 120 is used and the suture, after passing from eyesplices 44a and 44b is threaded through the holes in button 20 and though the 3rd and 4th holes in button 120.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:
1. A method of ankle syndesmosis repair, comprising:
preparing a bone tunnel through a fibula and a tibia of an ankle joint;
passing a first fixation device through the bone tunnel of the fibula and the bone tunnel of the tibia until the first fixation device exits on a medial side of the tibia;
flipping the first fixation device so it rests against a medial cortex of the tibia; and
positioning a second fixation device at a lateral side of the fibula, wherein the first fixation device and the second fixation device are knotles sly secured relative to the tibia and the fibula without tying knots,
wherein an adjustable loop is connected to the first fixation device and the second fixation device, and the adjustable loop includes at least one spliced section formed by splicing a strand of the adjustable loop through itself.

2. The method as recited in claim 1, comprising reducing a fracture of the fibula prior to preparing the bone tunnel through the fibula and the tibia.

3. The method as recited in claim 2, wherein reducing the fracture includes:
mounting a bone plate to the fibula.

4. The method as recited in claim 3, wherein passing the first fixation device includes:
pulling the first fixation device through an opening of the bone plate before entering the bone tunnel of the fibula.

5. The method as recited in claim 1, wherein passing the first fixation device includes:
connecting the first fixation device to a suture passing instrument with a suture; and
inserting the suture passing instrument through the bone tunnel to advance the first fixation device horizontally through the bone tunnel.

6. The method as recited in claim 5, wherein flipping the first fixation device includes:
pulling laterally on a portion of a flexible member connected to the first fixation device until the first fixation device moves from a position generally parallel to the bone tunnel to a position generally transverse to the bone tunnel.

7. The method as recited in claim 1, wherein positioning the second fixation device includes:
tightening the second fixation device down on the lateral side of the fibula by applying traction to a free strand of the adjustable loop that is connected to each of the first fixation device and the second fixation device.

8. The method as recited in claim 7, wherein applying the traction reduces a length of the adjustable loop to move the first fixation device and the second fixation device closer together.

9. The method as recited in claim 1, wherein the first fixation device includes a first configuration and the second fixation device includes a second configuration that is different from the first configuration.

10. A method of ankle syndesmosis repair, comprising:
attaching a bone plate to a fibula;
preparing a bone tunnel through the fibula and a tibia;
passing a first fixation device through the bone plate and then through the bone tunnel of the fibula and the bone tunnel of the tibia until the first fixation device exits on a medial side of the tibia;
flipping the first fixation device so it rests against a medial cortex of the tibia; and
cinching a second fixation device into place against the bone plate by applying traction to a portion of an adjustable loop connected to the first fixation device and the second fixation device,
wherein the adjustable loop includes at least one spliced section formed by splicing a strand of the adjustable loop through itself.

11. The method as recited in claim 10, wherein the first fixation device and the second fixation device are knotlessly secured relative to the tibia and the fibula, respectively, without tying knots.

12. The method as recited in claim 10, comprising reducing a fracture of the fibula using the bone plate.

13. The method as recited in claim 10, wherein attaching the bone plate includes:
mounting the bone plate to the fibula using a plurality of screws.

14. The method as recited in claim 10, wherein the first fixation device is oblong and the second fixation device is round.

15. The method as recited in claim 10, wherein cinching the second fixation device includes:
applying the traction to a free strand of the adjustable loop such that a length of the adjustable loop is reduced and the first fixation device and the second fixation device are moved closer together.

16. The method as recited in claim 10, wherein cinching the second fixation device includes:
positioning the second fixation device within an opening of the bone plate.

17. The method as recited in claim 10, wherein passing the first fixation device through the bone plate includes:
pulling the first fixation device through an opening formed through the bone plate.

18. The method as recited in claim 10, wherein the second fixation device includes at least four holes.

19. A method of ankle syndesmosis repair, comprising:
attaching a titanium bone plate to a fibula, wherein attaching the titanium bone plate includes positioning a first bone screw within a first opening of the titanium bone plate;
preparing a bone tunnel through the fibula and a tibia;
passing an oblong fixation device through the titanium bone plate and then through the bone tunnel of the fibula and the bone tunnel of the tibia until the oblong fixation device exits on a medial side of the tibia;
flipping the oblong fixation device so it rests against a medial cortex of the tibia; and
cinching a round fixation device into place within a second opening of the titanium bone plate by applying traction to a free strand of an adjustable loop that is connected to the oblong fixation device and the round fixation device,
wherein the oblong fixation device and the round fixation device are secured relative to the tibia and the fibula, respectively, without tying knots,
wherein the adjustable loop includes at least one spliced section formed by splicing a strand of the adjustable loop through itself,
wherein the free strand extends from the at least one spliced section of the adjustable loop,
wherein the second opening is located distally from the first opening once the titanium bone plate is attached to the fibula.

* * * * *

UNITED STATES PATENT AND TRADEMARK OFFICE
CERTIFICATE OF CORRECTION

PATENT NO. : 10,251,686 B2
APPLICATION NO. : 14/883890
DATED : April 9, 2019
INVENTOR(S) : Eric S. Zajac, Ricardo Albertorio and Brandon L. Roller Page 1 of 1

It is certified that error appears in the above-identified patent and that said Letters Patent is hereby corrected as shown below:

In the Claims

In Claim 1, Column 9, Line 1; replace "knotles sly" with --knotlessly--

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*